US008624589B2

(12) United States Patent
Puchot et al.

(10) Patent No.: US 8,624,589 B2
(45) Date of Patent: Jan. 7, 2014

(54) MAGNETOSTRICTIVE PROBES FOR SURFACE WAVE TESTING OF THICK WALLED STRUCTURES

(75) Inventors: Alan R. Puchot, San Antonio, TX (US); Charles E. Duffer, San Antonio, TX (US); Sang Y. Kim, San Antonio, TX (US); Adam C. Cobb, San Antonio, TX (US); Pavan K. Shukla, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 505 days.

(21) Appl. No.: 13/006,776

(22) Filed: Jan. 14, 2011

(65) Prior Publication Data

US 2011/0221428 A1     Sep. 15, 2011

Related U.S. Application Data

(60) Provisional application No. 61/312,593, filed on Mar. 10, 2010.

(51) Int. Cl.
*G01N 27/82* (2006.01)
*G01N 29/04* (2006.01)
*G01N 29/24* (2006.01)

(52) U.S. Cl.
CPC .......... *G01N 29/041* (2013.01); *G01N 29/2412* (2013.01)

USPC ............................................. 324/240; 73/620

(58) Field of Classification Search
USPC ............................................. 324/240; 73/620
See application file for complete search history.

(56) References Cited

U.S. PATENT DOCUMENTS

| 4,296,486 A * | 10/1981 | Vasile ........................... 367/140 |
| 6,924,642 B1 * | 8/2005 | Cho et al. ...................... 324/240 |
| 2009/0145239 A1 * | 6/2009 | Girshovich et al. ............. 73/779 |
| 2010/0052669 A1 * | 3/2010 | Kwun et al. ................... 324/240 |

FOREIGN PATENT DOCUMENTS

GB     2113392 A *     8/1983     ............. G01N 29/04

OTHER PUBLICATIONS

Shujuan Wang, et al., 3-D Modeling and Analysis of Meander-line-coil Surface Wave EMATS, Mechantronics 22 (2012) 653-660, available online May 31, 2011.

* cited by examiner

*Primary Examiner* — Jay Patidar
(74) *Attorney, Agent, or Firm* — Chowdhury & Georgakis P.C.; Ann C. Livingston

(57) ABSTRACT

An ultrasonic probe that uses the magnetostrictive effect to generate and detect a surface-coupled guided wave for the purpose of inspecting a thick-walled structure for surface defects. A transmitter sensor and a receiver sensor are especially designed to generate and detect short wavelengths that will couple to only one surface of the plate.

11 Claims, 3 Drawing Sheets

US 8,624,589 B2

MAGNETOSTRICTIVE PROBES FOR SURFACE WAVE TESTING OF THICK WALLED STRUCTURES

PRIORITY DATA

This application claims the filing date benefit of U.S. Application No. 61/312,593, filed Mar. 10, 2010.

TECHNICAL FIELD OF THE INVENTION

This invention relates to nondestructive testing of thick walled structures, and more particularly to use of a magnetostrictive sensor for such applications.

BACKGROUND OF THE INVENTION

Magnetostriction is a property of ferromagnetic materials that causes them to change shape when subjected to a magnetic field. Magnetostrictive materials can convert magnetic energy into kinetic energy, or the reverse, and are used to build various actuators and sensors.

Magnetostrictive sensors have been developed for nondestructive materials testing that make use of magnetostrictive properties of the material under inspection. Magnetostrictive sensors designed for testing ferromagnetic materials can also be made to work for testing nonferromagnetic metals by attaching a ferromagnetic material to the material being tested at areas where the sensors are to be placed. This may be achieved, for example, by coating the surface of the material to be tested with a coat of ferromagnetic material or by bonding a ferromagnetic medium such as wire or ribbon to the surface of the material.

The combination of a magnetized magnetostrictive material and an excitation coil produces a magnetostrictive sensor (MsS) probe. For active non-destructive testing, elastic waves are launched and reflected echoes of the waves from defects such as corrosion or cracks are detected. A typical application of an MsS probe is for inspecting pipes and tubes, the primary structural members used in various industries to transport gaseous or liquid products. Various MsS probes have been designed to generate longitudinal waves in rods and cables, torsional waves in pipes, and shear horizontal waves in plates.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

As indicated in the Background, MsS (magnetostrictive sensor) guided wave probes have been developed for testing plate structures, and do so by generating shear horizontal waves. These probes are well suited for monitoring structures with wall thicknesses up to 25 mm, but their principle of operation limits their operation on thicker structures. In order to apply MsS technology to thicker structures, a sensor capable of generating a surface guided wave is needed.

The following description is directed to an MsS sensor for monitoring thick-walled structures. The sensor detects corrosion and surface breaking cracks using an ultrasonic pitch-catch technique. As explained below, the sensor has a pair of probes (transmitter probe and receiver probe), which may be placed adjacent to each other along the wave propagation axis or may be separated by some distance on the inspection surface.

Previously developed MsS probes use a time varying magnetic field, and have a thin ferromagnetic strip and an electrical coil. The strip is mechanically bonded to the test structure and is magnetized. The electrical coil is placed over the strip, and an alternating current pulse is applied to the coil. The current induces a time-varying magnetic field, which produces a time-varying strain in the ferromagnetic strip. As a result, ultrasonic waves are generated by the probe and are mechanically coupled into the test structure. Both the type and frequency of the generated waves depend upon the frequency of the applied current, the orientation of the driving forces caused by the magnetic fields induced by the probe, and the wall thickness of the material being inspected.

Figure 1:
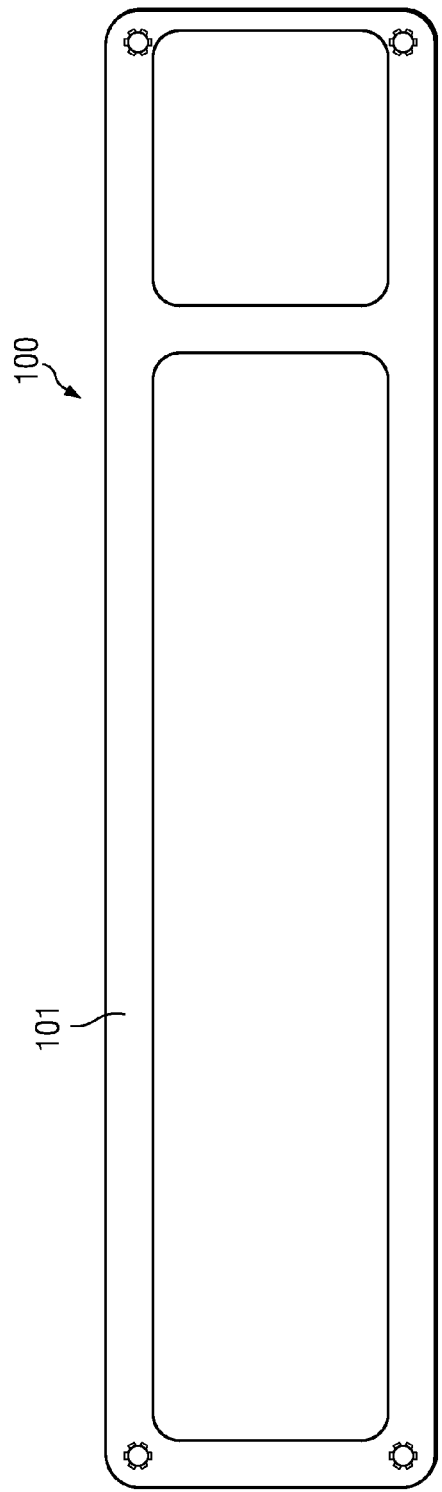
FIG. 1 is a top view of the probe housing with the lid removed.
Figure 2:
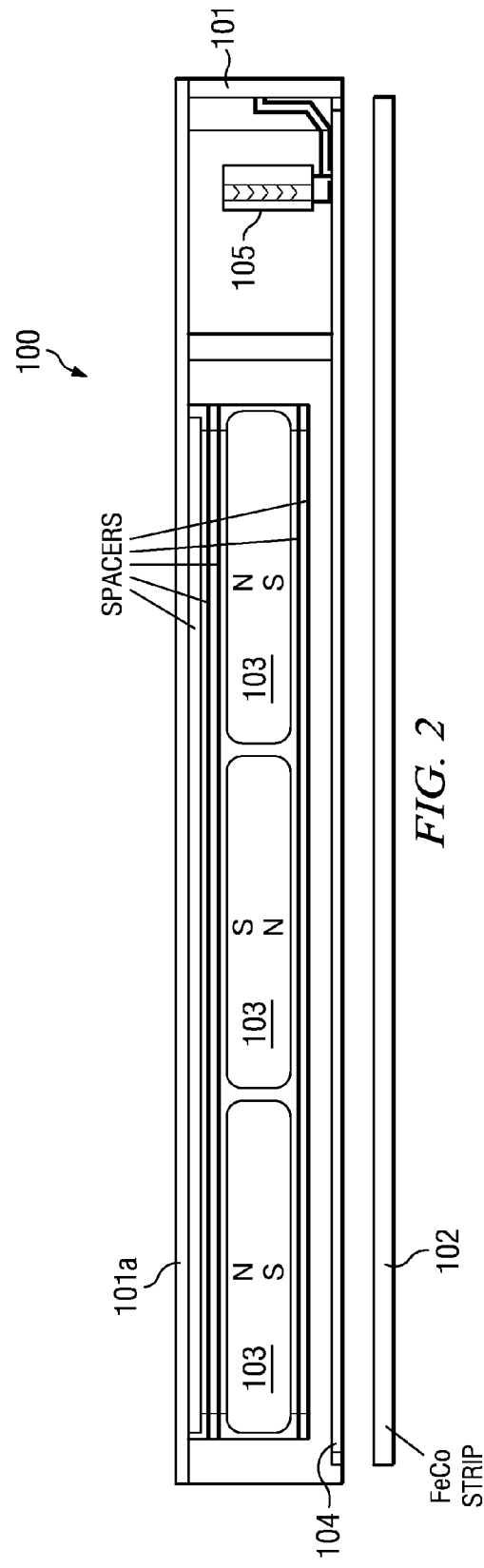
FIG. 2 is a cut away view of the probe to illustrate the major components.

FIGS. 1 and 2 illustrate an MsS probe 100 in accordance with the invention. FIG. 1 is a top plan view of the probe housing 101 with its lid removed from the top of the probe. FIG. 2 is a sectional side view of the probe 100, to illustrate its major components.

For testing thick-walled structures, probe 100 relies on the generation of a wave with a wavelength much smaller than the thickness of the inspected structure. An objective is to couple the wave to only one surface of the inspected structure. To generate the surface wave, both a time-varying magnetic field and a time-invariant magnetic field are induced within a ferromagnetic strip 102, which serves as the ultrasonic actuator of the probe 100. The time-invariant field is induced nominally through the thickness of the strip 102. The time-varying field is induced nominally parallel to the surface of the strip 102 and along the wave propagation axis.

Figure 3:
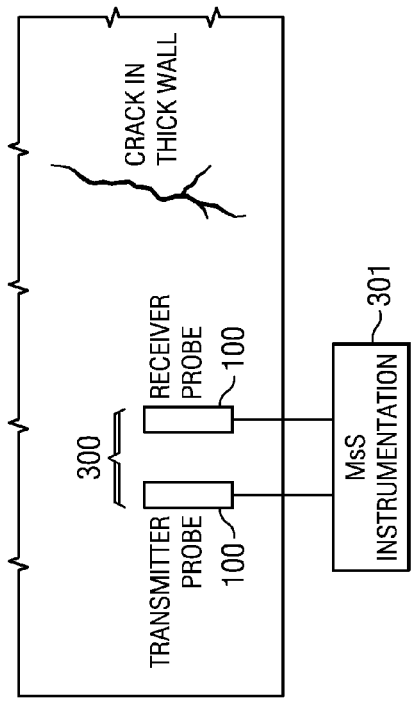
FIG. 3 illustrates both a transmitter probe and a receiver probe in place for testing a thick walled structure.

Referring to FIG. 3, a complete MsS sensor 300 has two probes 100, and is shown in place on the surface of a thick walled structure for detecting defects in the structure wall. The surface under test is generally planar. A first probe 100 (transmitter) transmits a surface wave at a given frequency. An example of a typical frequency is 500 kHz. A second probe 100 (receiver) detects the transmitted wave and subsequent reflections, and is designed to produce the greatest possible signal response to the detected signals.

An MsS instrumentation unit 301 is used for providing driver (activation) signals to the transmitter probe 100, and for receiving surface wave (response) signals from the receiver probe 100. The instrumentation unit 301 has appropriate circuitry for performing these functions, and may also have hardware and software for performing analysis and reporting of the received signals. In operation, a reference waveform may be subtracted from each subsequent monitoring waveform to produce a differential waveform.

Referring again to FIGS. 1 and 2, the transmitter probe 100 and the receiver probe 100 each have five major elements: (i) a thin ferromagnetic strip 102 with a large coefficient of magnetostriction, (ii) a set of permanent magnets 103 to bias the ferromagnetic strip, (iii) an electronic coil 104 to drive a time-varying magnetic field in the ferromagnetic strip, (iv) a capacitor 105 to match the input impedance of the probe to the impedance expected by the probe driver instrument, and (v) a housing 101 to house the other probe elements and minimize the effect of external electromagnetic noise.

The probe elements (ii) through (iv) are enclosed in housing 101. A top plate 101a is part of housing 101. As indicated in FIGS. 1 and 2, the magnets 103, coil 104, and strip 102 are generally rectangular and planar, with a thickness much smaller than their length or width. They are arranged in layers, with the strip 102 being exposed on the bottom of housing 101 so that strip 102 can be placed against the surface being tested.

An example of a suitable material for strip 102 is an iron cobalt (FeCo) alloy. The ferromagnetic strip 102 may be adhered to the inspection surface, using an adherent such as epoxy.

The transmitter probe 100 and receiver probe 100 may be nearly identical in construction, with the exception of the electronic coil 104 and the impedance-matching capacitor 105. The receiver probe 100 requires a large number of windings within the coil 104 and relatively high characteristic impedance in order to produce a large voltage response to a detected signal. The transmitter probe 100 requires a much lower characteristic impedance to generate the surface wave.

Figure 4:
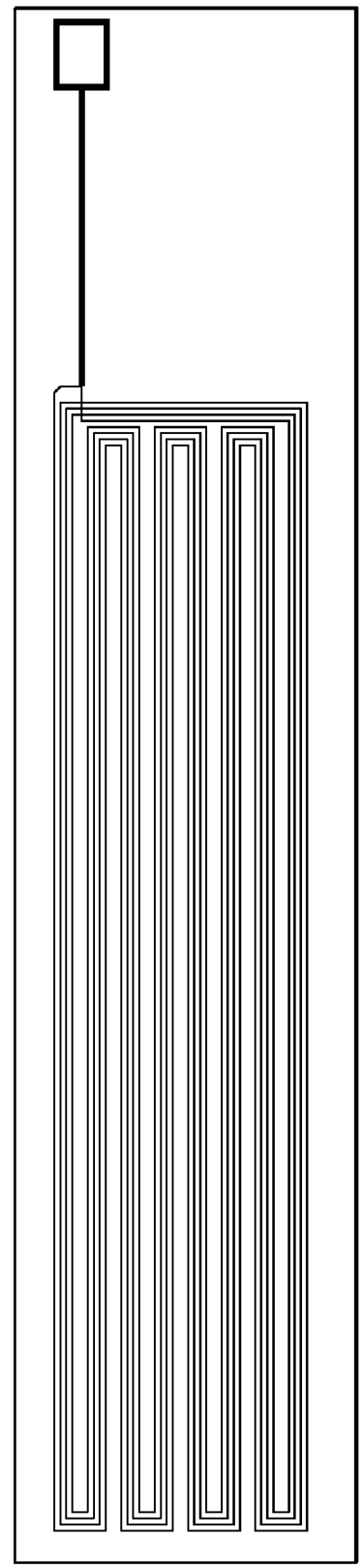
FIG. 4 illustrates an example of the coil.

FIG. 4 illustrates an example of the coil 104. An example of a suitable coil 104 to generate surface waves for use in ultra-high frequency applications is a meanderline coil. The coil 104 is modular and multilayer, to satisfy the requirements of both probes. Each coil layer is printed on a flexible kapton sheet with one contact on either side of the sheet. The receiver probe 100 uses two coils 104 stacked vertically to form a single series multi-layer coil, whereas the transmitter probe 100 uses a single coil 104.

An example of suitable coil dimensions is 102 mm×25 mm (4 inches×1 inch). The coil 104 of FIG. 4 is a single layer 500 kHz meanderline coil. It has four meanderline repetitions, each with four wire traces.

The coil 104 in both the transmitter probe 100 and the receiver probe 100 behaves essentially as an inductor. The ferromagnetic strip 102 behaves as an inductor core. Therefore, the impedance of the coils 104 has a very large imaginary component. To match the impedance of the probes 100 to the impedance values expected by the MsS driver instrument, the transmitter capacitor 105 has a capacitance that will place the transmitter coil in series resonance, and the receiver capacitor 105 has a capacitance that will place the receiver coil in parallel resonance. Examples of typical capacitance values are 27 nF and 9 nF for the transmitter and receiver capacitors, respectively. The transmitter coil can drive the largest possible current due to an applied voltage, and the receiver coil can drive the largest possible voltage due to an induced current. This allows both probes 100 to perform with optimum efficiency.

The remaining elements are identical for both probes 100. The bias magnets 103 are placed over the coil 104, which is placed over strip 102, relative to the surface being tested. The magnetic bias field generated by magnets 103 is generally perpendicular to the surface being tested, and passes nominally through the thickness of strip 102.

In the example of FIG. 2, probe 100 has three magnets 103. The magnets are grade N42 neodenium iron boron magnets 103, measuring 38.1 mm×19.1 mm×6.4 mm [1.5 in×0.75 in×0.25 in]. The north-to-south field direction is aligned through the 6.4 mm thickness of each magnet 103. The magnet 103 in the center is oriented with the poles opposite the direction of the adjacent (side) magnets 103. Alternatively, two magnets with their respective poles placed in opposite orientations could be used.

The body of the probe housing 101 is composed of aluminum, and a carbon steel top plate 101a is included on the probe. The enclosure 101 serves to maintain the positioning of the other probe elements, and doubles as an electronic noise shield. Various other noise-shielding materials may be used for housing 101 and lid 101a.

Figure 5:
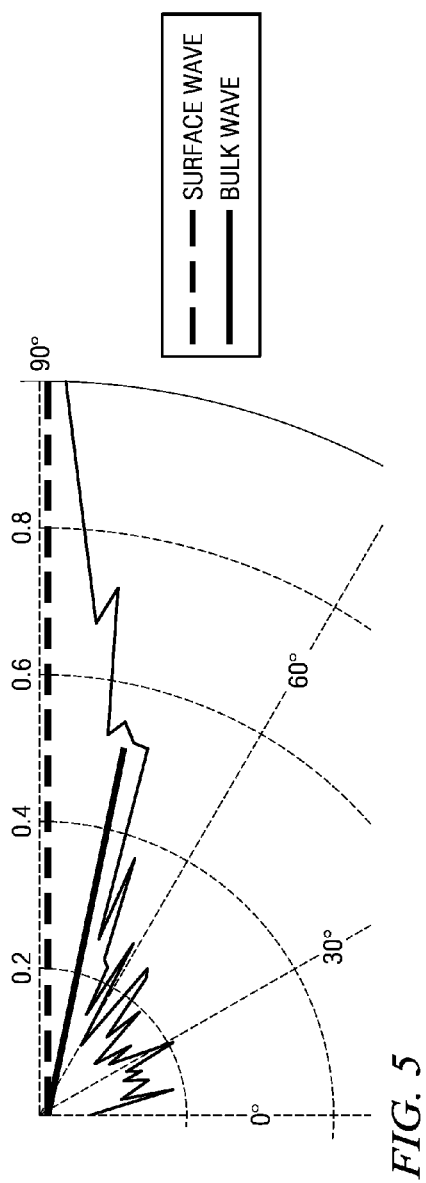
FIG. 5 illustrates a normalized radiation pattern of the transmitter probe through the thickness of the inspection surface.

FIG. 5 illustrates a normalized radiation pattern of the transmitter probe through the thickness of the inspection surface. In the example of FIG. 5, the wave propagation properties of two MsS probes 100 were characterized on a 50 mm thick carbon steel plate. The majority of the energy generated by the transmitter probe travels as a surface wave and is bounded within the first 1.5 wavelengths {8.9 mm [0.35 in]} of the plate surface. Most of the remaining energy is transmitted as a bulk wave at a 16° incidence relative to the plate surface.

In FIG. 5, the primary lobe is bounded between an incidence angle of 82° and 90°. A significant secondary lobe is observed to peak at roughly 74°. This secondary lobe propagates as a bulk wave.

Figure 6:
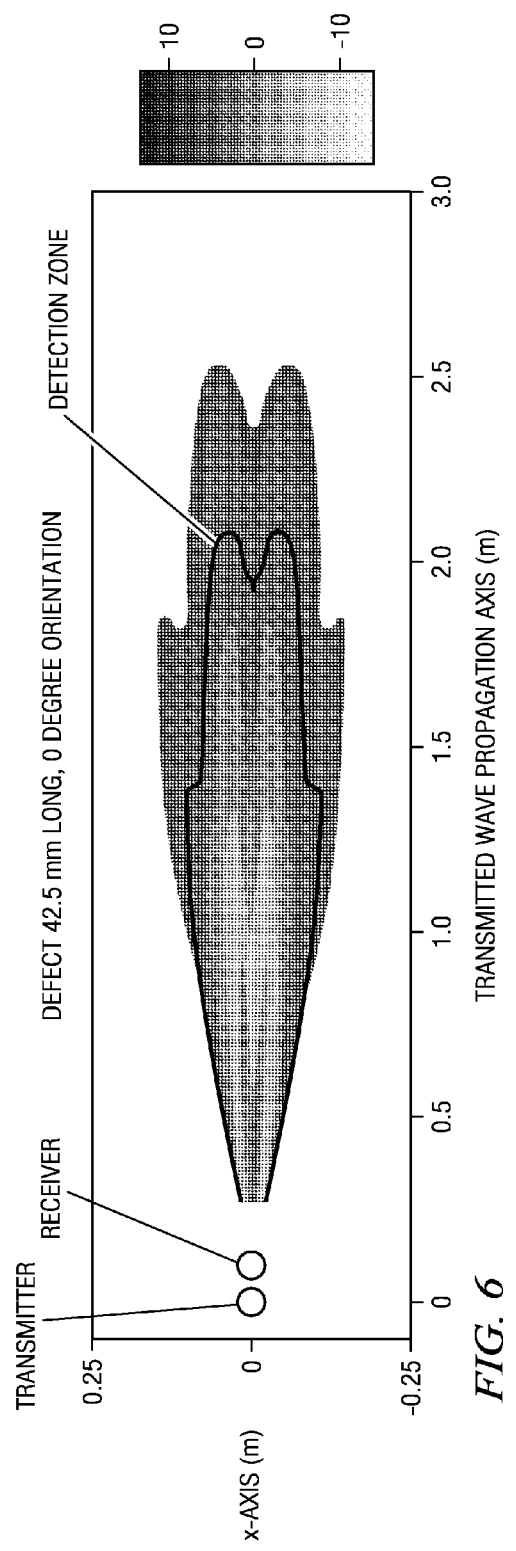
FIG. 6 illustrates a detection map, resulting from experimental testing to determine the defect detection sensitivity of the sensor.

FIG. 6 illustrates a detection map, resulting from experimental testing to determine the defect detection sensitivity of the sensor to a defect measuring 12.5 mm [0.49 in] deep, 42.5 mm [1.67 in] long, and 200 μm [7.9 mils] wide. The testing was conducted with the transmitter probe and receiver probe separated by 100 mm, and with the receiver probe centered on the wave propagation axis.

The useful detection zone of FIG. 6 assumes a 10 cm [3.93 in] separation between the transmitter probe (blue circle) and the receiver probe (red circle). The area of the detection zone that is deemed reliable is bounded by a black outline. At a distance of 2 m [6.56 ft], the useful detection zone is roughly 16 cm [6.3 in] wide. At the widest point, {1.35 m [4.43 ft]} the zone is roughly 24 cm [9.45 in] wide. The near field of the probe, which extends roughly 44 cm [17.32 in] from the transmitter probe, is not depicted.

In experimental use, a sensor 300 comprising a pair of probes 100 has been shown to propagate a surface guided wave on structures exceeding 25 mm in thickness and have been demonstrated for crack detection. The sensor 300 has been shown to be capable of detecting large cracks exceeding 1 cm in depth and 4 cm in length at distances up to 2 meters from the receiver probe, and can detect cracks as small as 1 mm in depth and 1 cm in length at distances less than 1 m from the receiver probe. The sensor 300 is designed to monitor the structural integrity of thick-walled structures, such as dry storage cask systems for nuclear waste, pressure vessels in the chemical and petrochemical industries, nuclear containment shells, and structural plating on oil tankers.

The invention claimed is:

1. A magnetostrictive probe for testing for defects in a thick walled structure, comprising:
    a set of magnets configured to induce a time invariant magnetic field;
    and at least one electric coil configured to induce a time varying magnetic field when activated with an activation signal;
    a strip of magnetostrictive material;
    wherein the magnets are arranged such that their polarity is normal to the surface of the structure and such that the time invariant field is through the thickness of the strip and to the surface of the structure;

wherein the coil is a meanderline coil arranged parallel to the surface of the structure and such that the time varying field is generally parallel to the surface; and wherein the magnet, coil, and the strip are layered, such that when the strip is placed against the surface, the coil is above the strip and the magnet is above the coil.

2. The probe of claim 1, wherein the probe has at least two magnets and at least one magnet is oriented with its polarization opposite that of another.

3. The probe of claim 1, further comprising a housing for containing the magnets and the coil, and wherein the strip is adjacent the bottom of the housing.

4. The probe of claim 1, wherein, when the coil is activated with the activation signal, the probe is operable to produce a surface wave coupled to the surface.

5. A magnetostrictive probe for testing for defects in a thick walled structure, comprising:
   a set of magnets configured to induce a time invariant magnetic field;
   and at least one electric coil configured to induce a time varying magnetic field when activated with an activation signal;
   a strip of magnetostrictive material;
   wherein the time invariant field is through the thickness of the strip and to the surface of the structure;
   wherein the time varying field is generally parallel to the surface; and
   wherein the magnet, coil, and the strip are layered, such that the strip may be placed against the surface, with the coil above the strip and the magnet above the coil;
   further comprising a capacitor electronically connected to the strip, configured to match impedance of the probe to impedance of equipment used to deliver activation signals to the probe or to receive response signals from the probe.

6. A magnetostrictive probe for testing for defects in a thick walled structure, comprising:
   a set of magnets configured to induce a time invariant magnetic field;
   and at least one electric coil configured to induce a time varying magnetic field when activated with an activation signal;
   a strip of magnetostrictive material;
   wherein the time invariant field is through the thickness of the strip and to the surface of the structure;
   wherein the time varying field is generally parallel to the surface; and
   wherein the magnet, coil, and the strip are layered, such that the strip may be placed against the surface, with the coil above the strip and the magnet above the coil;
   further comprising a capacitor electronically connected to the strip, configured to match impedance of the probe to impedance of equipment used to deliver activation signals to the probe or to receive response signals from the probe.

7. A method of generating a surface wave for testing a thick walled structure, comprising:
   placing a transmitting magnetostrictive probe on the surface of the structure;
   wherein the probe comprises the following elements: a set of magnets configured to induce a time invariant magnetic field, at least one electric coil configured to induce a time varying magnetic field when activated with an activation signal, and a strip of magnetostrictive material; wherein the magnet, coil, and the strip are layered, such that when the strip is placed against a surface of the structure, the coil is above the strip and the magnet is above the coil;
   wherein the magnets are arranged such that their polarity is normal to the surface of the structure such that the time invariant field is through the thickness of the strip and to the surface of the structure;
   wherein the coil is a meanderline coil arranged parallel to the surface of the structure such that the time invariant field is generally parallel to the surface;
   wherein the probe, when the coil is activated, is operable to produce a surface wave coupled to the surface; and
   activating the transmitting magnetostrictive coil.

8. The method of claim 7, wherein the probe has at least two magnets, and at least one magnet is oriented with its polarization opposite that of another.

9. The method of claim 7, wherein the set of magnets is oriented such that its magnetic field is generally vertical to the surface of the structure.

10. The method of claim 7, wherein the coil, when activated, produces a time varying field that is generally parallel to the surface.

11. The method of claim 7, wherein the activation signal has a wavelength less than the thickness of the structure.

* * * * *